United States Patent
McCall

(10) Patent No.: US 9,526,669 B1
(45) Date of Patent: Dec. 27, 2016

(54) SEXUAL MOUTH GUARD

(71) Applicant: Picolya McCall, Long Beach, CA (US)

(72) Inventor: Picolya McCall, Long Beach, CA (US)

( * ) Notice: Subject to any disclaimer, the term of this patent is extended or adjusted under 35 U.S.C. 154(b) by 202 days.

(21) Appl. No.: 14/294,118

(22) Filed: Jun. 2, 2014

Related U.S. Application Data

(60) Provisional application No. 61/829,247, filed on May 31, 2013.

(51) Int. Cl.
*A61F 5/00* (2006.01)
*A61H 19/00* (2006.01)
*A63B 71/08* (2006.01)

(52) U.S. Cl.
CPC .............. *A61H 19/00* (2013.01); *A63B 71/085* (2013.01)

(58) Field of Classification Search
CPC ........ A63B 71/08; A63B 71/085; A61F 5/566
USPC ................................ 600/38–41; 128/859–862
See application file for complete search history.

(56) References Cited

U.S. PATENT DOCUMENTS

| | | | | |
|---|---|---|---|---|
| 2,857,909 | A * | 10/1958 | Johnson | A63B 71/085 128/861 |
| 4,114,614 | A * | 9/1978 | Kesling | A63B 71/085 128/861 |
| 6,886,567 | B1 * | 5/2005 | Liu | A63B 71/085 128/848 |
| 7,798,149 | B2 * | 9/2010 | Haduong | A61F 5/566 128/845 |
| 2007/0151568 | A1 * | 7/2007 | Maurello | A63B 71/085 128/859 |
| 2008/0053463 | A1 * | 3/2008 | Enoch | A61F 5/566 128/861 |
| 2008/0289638 | A1 * | 11/2008 | Peters | A61F 5/566 128/861 |

* cited by examiner

*Primary Examiner* — John Lacyk
(74) *Attorney, Agent, or Firm* — Kafantaris Law Offices; Theo Kafantaris

(57) ABSTRACT

The present invention provides a thin elastomeric mouth guard which covers the teeth to provide a smooth surface during oral sex. The mouth guard will feature different colors and flavors to enhance lubrication and to promote a more enjoyable experience for both the giving and receiving party. Furthermore, it may encourage parties to engage in oral sex, as it reduces risk and discomfort.

12 Claims, 5 Drawing Sheets

SEXUAL MOUTH GUARD

CROSS-REFERENCE TO RELATED APPLICATIONS

This application claims the benefit of U.S. Provisional Patent Application No. 61/829,247, filed on May 31, 2013, and incorporated herein by reference.

STATEMENT REGARDING FEDERALLY SPONSORED RESEARCH AND DEVELOPMENT

Not Applicable.

FIELD OF THE INVENTION

This invention relates generally to a sexual mouth guard, and more particularly, to a mouth guard for covering teeth during oral sex.

DISCUSSION OF RELATED ART

Oral sex can generally be described as sexual activity where the genitalia of the receiving party are stimulated by the mouth, tongue, teeth, or throat of the giving party. When performed on a male, oral sex is defined as fellatio, and when performed on a female, oral sex is defined as cunnilingus. Oral sex is generally used as a part of foreplay before sexual intercourse, or can replace intercourse altogether.

Mouth guards can generally be described as protective devices for the mouth, teeth, tongue, and gums. Mouth guards are commonly used during contact sports such as football, where the impact of the collisions could easily cause damage the mouth and teeth of the players. Mouth guards can also be used after dental procedures to protect the teeth or encourage dental alignment.

While several different mouth guards are known in the art, they are intended for either contact sport or dental use. As such, they are often bulky, or do not provide adequate coverage and protection for the teeth. Furthermore, there are few devices in the art which are used by the giving party to protect the receiving party during oral sex. Therefore, a need exists for a thin mouth guard which covers the teeth to provide a smooth surface during oral sex. The present invention satisfies these needs.

SUMMARY OF THE INVENTION

The present invention provides a thin elastomeric mouth guard which covers the teeth to provide a smooth surface during oral sex. The mouth guard will feature different colors and flavors to enhance lubrication and to promote a more enjoyable experience for both the giving and receiving parties. The device may be a one-time-use product or be designed for multiple uses depending upon the materials used. Furthermore, it may encourage parties to engage in oral sex, as it reduces risk and discomfort. The device may feature additional substances to increase sensation and textures to increase comfort and satisfaction.

In the preferred embodiment, the mouth guard comprises a top guard which removably fits over the upper teeth of the giving party. The top guard is made from a soft, deformable material that holds itself elastically to the upper teeth. The mouth guard further comprises a bottom guard which removably fits over lower teeth of the giving party, also made from a soft, deformable material that holds itself elastically to the lower teeth. Each guard is made from a single piece of molded elastomeric material.

In an alternative embodiment, the top and bottom guards mentioned above would be connected at each end by an elastic material designed to gently force the top and bottom guards against the respective sets of teeth. Here, both guards and the connective material would be molded together to form a single piece.

It is an objective of the present invention to provide a removable, sanitary means for eliminating abrasion and scratching during oral sex by providing a wearable oral device that attaches to the teeth. It is another objective to provide a device that remains stable during oral sex in order to avoid detracting from the enjoyment of the event. It is also an objective to increase the enjoyment of the wearer by providing a soft material that is flavored. As an added benefit, the flavoring will stimulate saliva production, which will improve the sensations of the oral sex recipient. It is also an objective of the present invention to provide the availability of a variety of tactile sensations for the recipient.

These and other objectives of the present invention will become obvious to those of ordinary skill in the art after reading the following detailed description of the preferred embodiments. It is to be understood that the foregoing general description and the following detailed description are exemplary, and are intended to provide further explanation of the invention as claimed.

DETAILED DESCRIPTION OF THE PREFERRED EMBODIMENT

Figure 1:
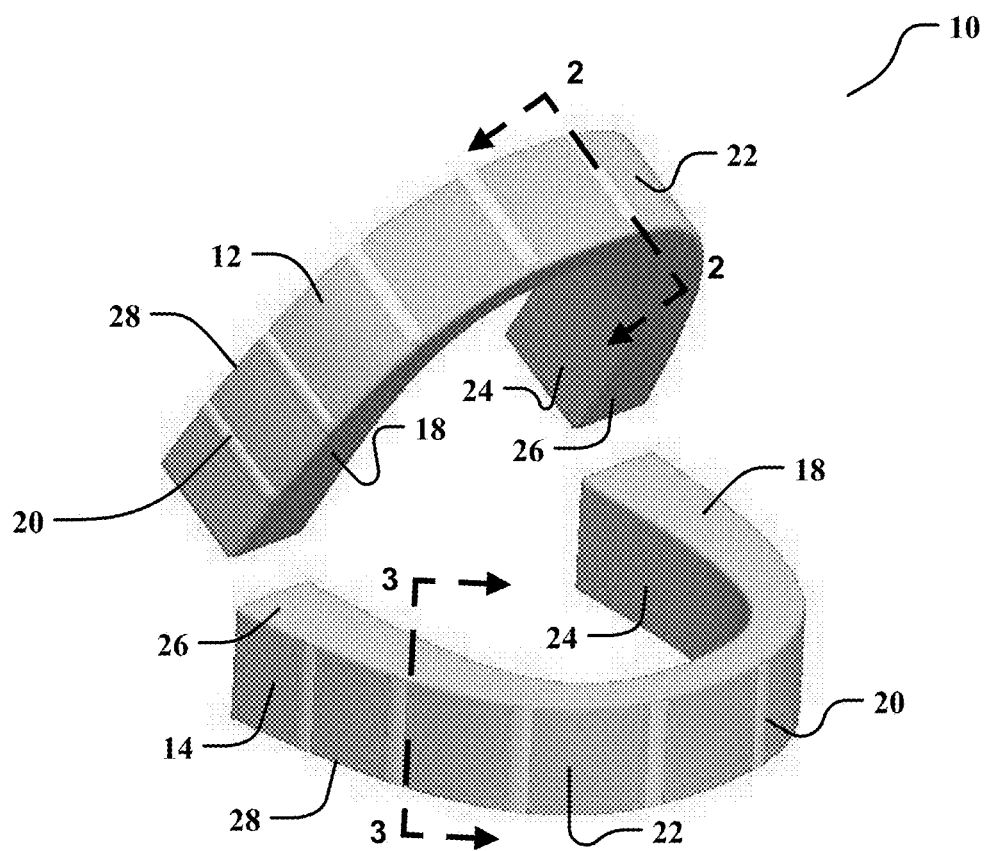
FIG. 1 is a front perspective view of the present invention.
Figure 2:
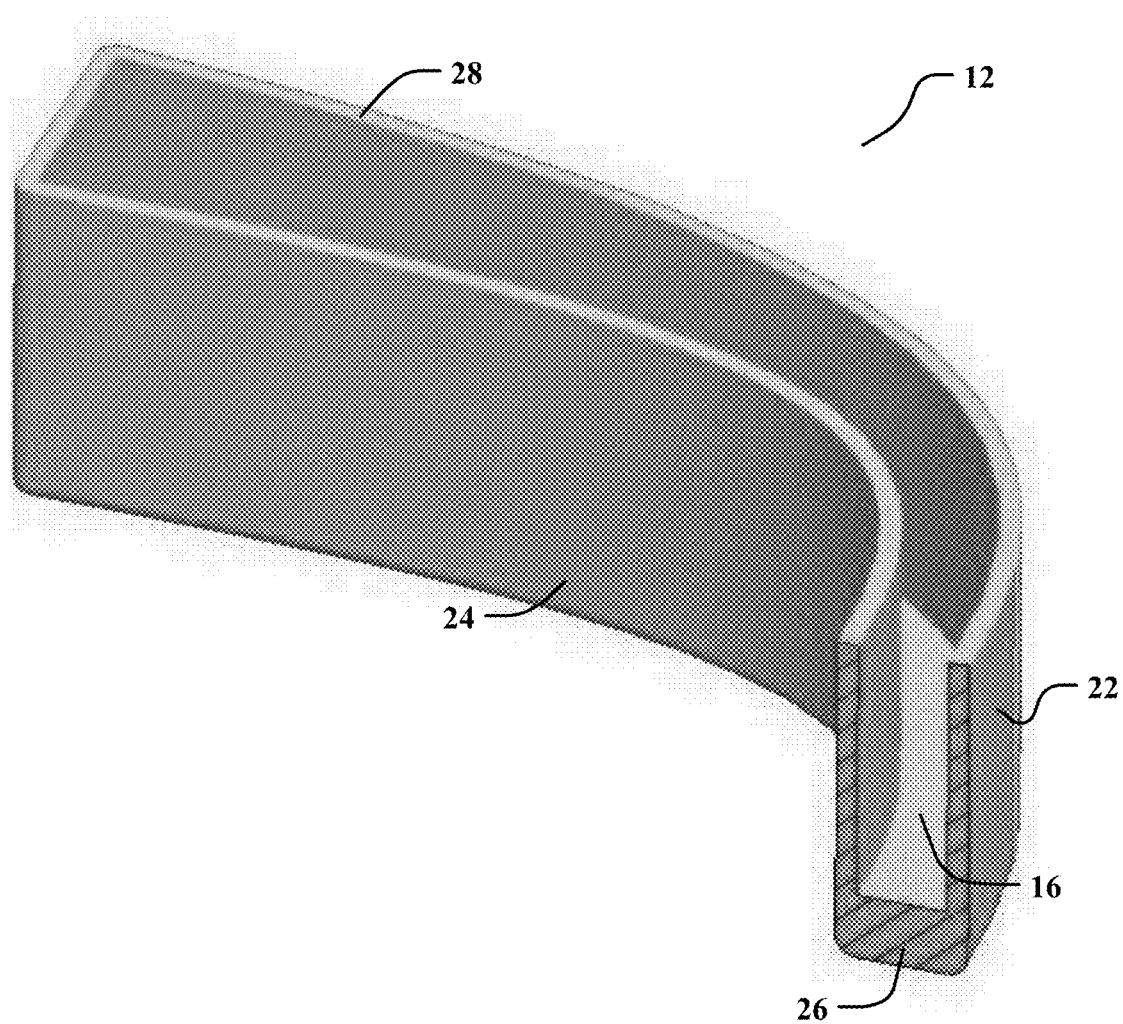
FIG. 2 is a cross-sectional view of the bottom guard along line 2-2 of FIG. 1.
Figure 3:
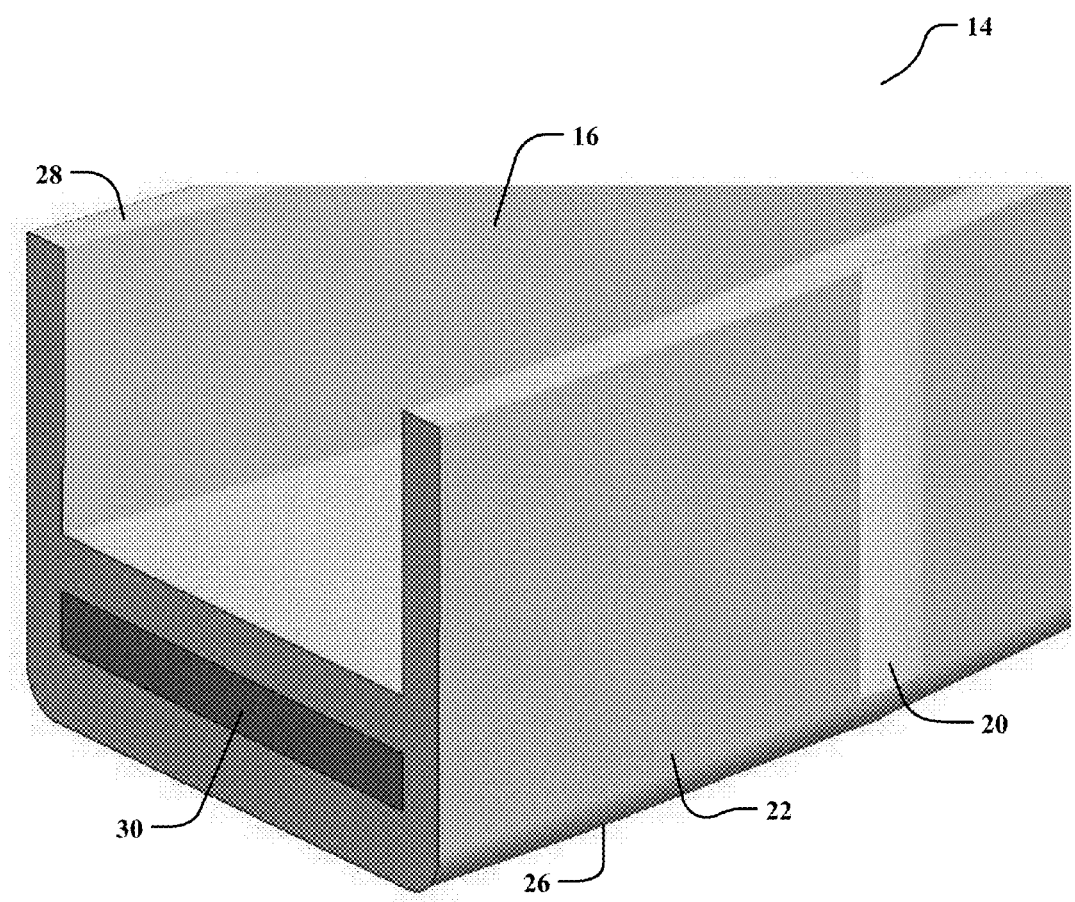
FIG. 3 is a cross-sectional view of the bottom guard along line 3-3 of FIG. 1.
Figures 4, 5:
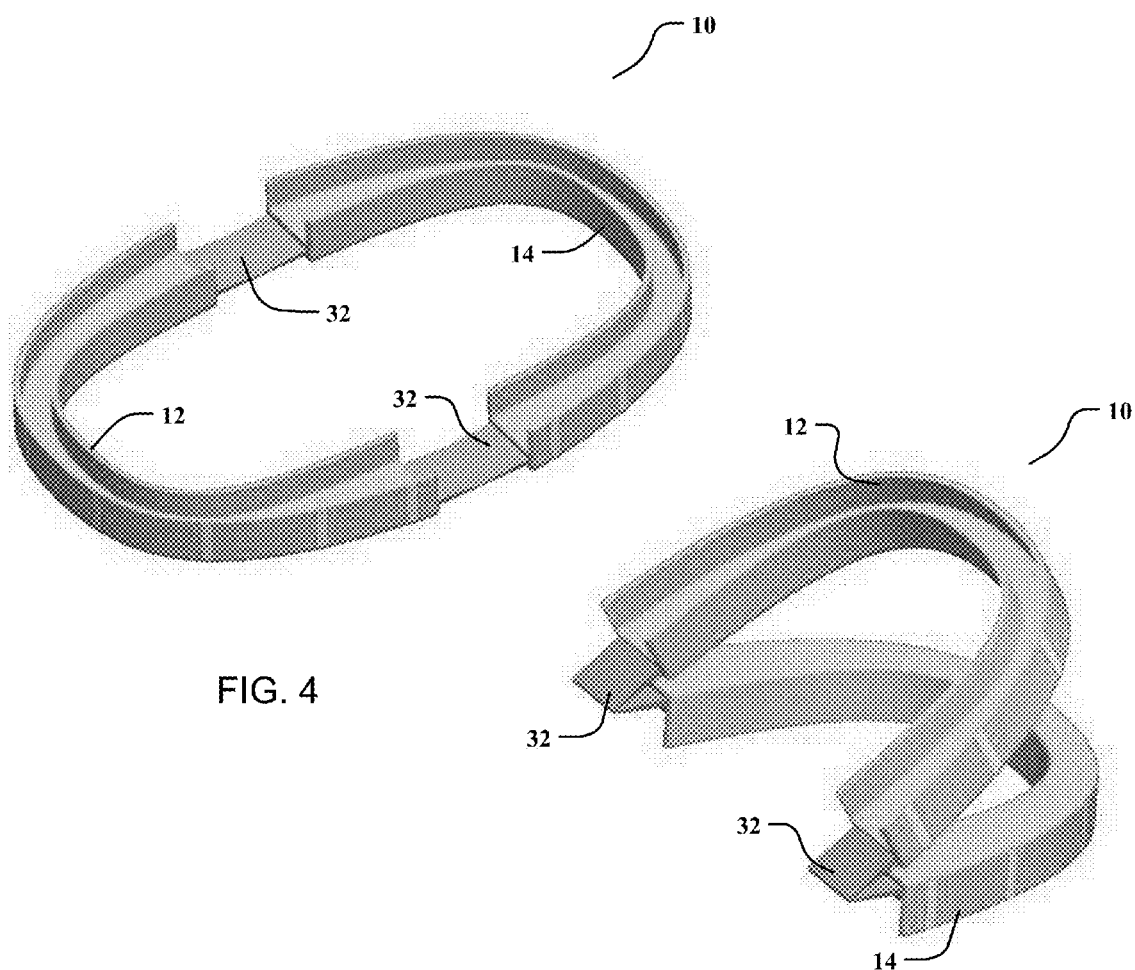
FIG. 4 is a perspective view of an alternative embodiment in an open position.
FIG. 5 is a perspective view of an alternative embodiment in a closed position.
Figure 6:
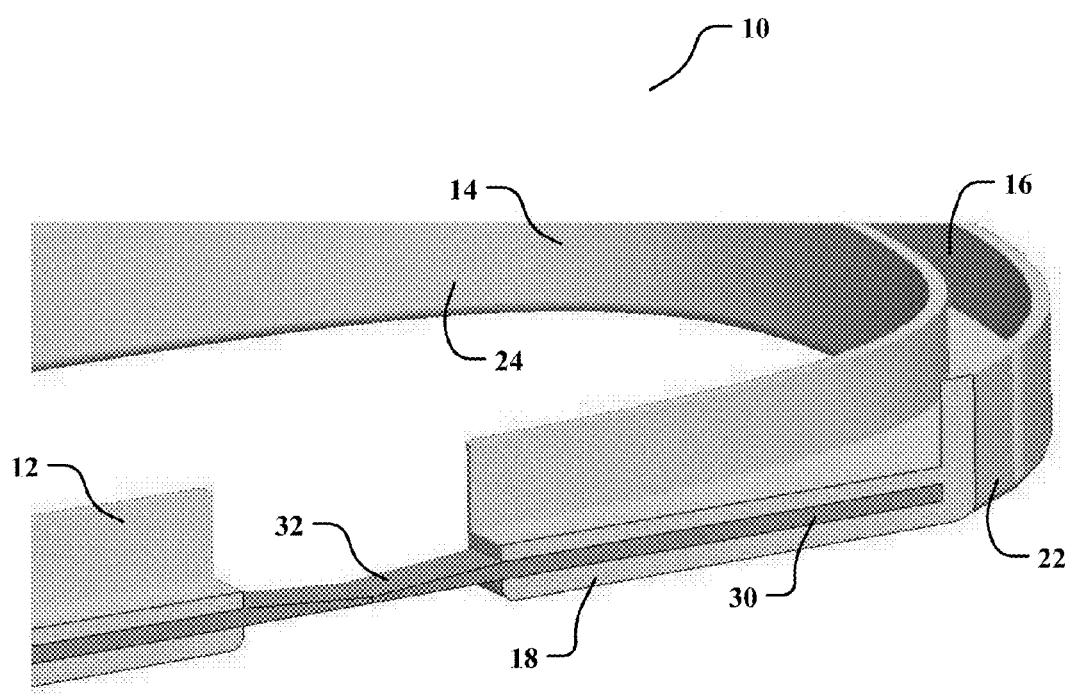
FIG. 6 is a close-up view of the pivotal attachment of the substrate in an alternative embodiment.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

The present invention comprises a mouth guard 10 intended to protect male genitalia during oral sex. This is accomplished by encapsulating the teeth of the giving party in a soft material such that the receiving party is protected from knicks, scratches, bites, etc. In the preferred embodiment, the present invention comprises a top guard 12 and a bottom guard 14, each having a generally U-shape. Each guard 12, 14 is formed or molded as a single piece and adapted to cover all of the giving party's teeth, including hard to reach posterior teeth.

The guards 12, 14 will each further comprise a facial side (near the cheek and lips) 22, a lingual side (near the tongue) 24, a coronal side (near the crowns of the teeth) 26, and an apical side (near the roots of the teeth) 28. The guards 12, 14 will further comprise a channel 16 adapted to receive the maxillary and mandibular teeth of the giving party. In the preferred embodiment, the channel 16 is flexible enough to receive the teeth but firm enough to provide a compression force to help retain the guards 12, 14 in the mouth of the giving party.

The guards 12, 14 will be made of an elastomeric material. Suitable materials comprise latex, silicone rubber, food grade elastomer, dental grade elastomer, or any other biologically stable elastomer. The elastomeric material will be durable and easily sanitized, as well as being resistant to deforming from repeated use. The thickness of the elastomer may vary from 0.1-10 mm, but it will not be so thick as to prevent or inhibit the administration of oral sex. The film will be adapted to fit around the teeth of the giving party, with the outer surface 18 having a soft texture for additional comfort. In an alternative embodiment, the present invention is adapted to mold to the teeth of the giving party during centric occlusion (biting down), both with and without external heat.

The guards 12, 14 further comprise a plurality of rigid, anti-flex members 20 positioned on the facial sides 22 between the coronal 26 and apical 28 sides. The anti-flex members 20 are adapted to prevent the mouth guard from twisting or otherwise deforming during administration of oral sex. The anti-flex members 20 become especially important as thinner elastomeric materials are used, as the motion will easily displace the guards 12, 14 from their intended positions. In an alternative embodiment, anti-flex members 20 are also positioned on the lingual side 24 for additional stability.

The present invention will be manufactured in several colors for added impact during performance and for marketing purposes, as well as a glow-in-the-dark variant for heightened appeal. Additionally, flavoring may be added to the device to appease the giving party. Flavoring will generally match the color of the invention. Combinations comprise a purple color and grape flavoring, a red color and cherry flavoring, a green color and apple flavoring, and a yellow color and banana flavoring. While these combinations are listed here, other color/flavor combinations may be used. In addition to flavoring, the device may be coated or layered with a substance 18 to increase sensation, such as a soft, flexible material, a hot-cold sensation, or a tingling sensation. Lastly, the device may be textured or ribbed to add increased sensation to the receiving party.

In an alternative embodiment, a substrate 30 is positioned within the top and bottom guards 12, 14 parallel to the coronal side 26. The substrate 30 comprises a stiff, rigid material such as dental grade plastic. The substrate 30 will help form the guards 12, 14 to the teeth and prevent twisting or accidental removal during use. This is accomplished through a pivotal attachment 32 between the top and bottom guards 12, 14. The pivotal attachment 32 operates as a spring hinge, which presses the top and bottom guards 12, 14 against the maxillary and mandibular teeth, respectively. The substrate 30 is completely enclosed within the top and bottom guards 12, 14, but the pivotal attachment 32 is exposed.

In a further alternative embodiment, the present invention comprises an inner mouth guard and an outer sheath that encloses the inner mouth guard, both in the top and bottom portions 12, 14. Here, the inner mouth guard will be made of a material capable of being molded using heat. The outer sheath may be manufactured in several colors and flavors, and may be coated in a substance for sensation or textured to increase stimulation. In contrast to the preferred embodiment, the inner mouth guard will not be discarded after use, with the outer sheath being discarded instead.

The present invention is intended to be in direct contact with the genitalia and mouth of the giving and receiving parties, respectively. As such, the present invention must be manufactured in a sterile environment and packaged such that no outside elements may come in contact with present invention after packaging. In the preferred embodiment, the present invention will be wrapped with packaging that can easily be opened through tearing, but will resist the normal wear and tear of shipping and storage in a purse or wallet. Furthermore, the packaging will clearly label the invention and flavoring, as well as any other features which aid in sensation and pleasure.

While the above description contains specific details regarding certain elements, sizes, and other teachings, it is understood that embodiments of the invention or any combination of them may be practiced without these specific details. Specifically, although certain materials and shapes are designated in the above embodiments, any suitable material or shape may be used. These details should not be construed as limitations on the scope of any embodiment, but merely as exemplifications of the presently preferred embodiments. In other instances, well known structures, elements, and techniques have not been shown to clearly explain the details of the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A sexual mouth guard comprising:
   a top guard having a generally U-shape;
   a bottom guard having a generally U-shape;
   said top and bottom guards further comprising a facial side, a lingual side, a coronal side, and an apical side;
   said top and bottom guards further comprising a channel adapted to receive the maxillary and mandibular teeth of the giving party;
   a plurality of rigid anti-flex support members positioned only on said facial sides between said coronal and said apical sides;
   wherein said sexual mouth guard is adapted to cover all of the giving party's teeth so as to protect the receiving party's genitalia during oral sex, and wherein said anti-flex support members are adapted to support said mouth guard vertically and prevent said mouth guard from twisting during oral sex.

2. The sexual mouth guard of claim 1, wherein said top and bottom guards further comprise an elastomeric material.

3. The sexual mouth guard of claim 2, wherein said elastomeric material is silicone rubber.

4. The sexual mouth guard of claim 2, wherein said elastomeric material is flavored.

5. The sexual mouth guard of claim 2, wherein said elastomeric material is colored.

6. The sexual mouth guard of claim 2, wherein said elastomeric material is adapted to conform to the shape of the giving party's teeth when pressed against one another during centric occlusion when external heat is added.

7. The sexual mouth guard of claim 2, wherein said elastomeric material is adapted to conform to the shape of the giving party's teeth when pressed against one another during centric occlusion without external heating.

8. The sexual mouth guard of claim 1, wherein said coronal side further comprises a soft, flexible material.

9. The sexual mouth guard of claim 1, wherein said coronal side further comprises a textured material.

10. The sexual mouth guard of claim 1, further comprising a substrate positioned within said top and bottom guards parallel to said coronal side.

11. The sexual mouth guard of claim 10, wherein said substrate is pivotally attached between said top and bottom guards, wherein said substrate operates as a spring hinge to hold said top and bottom guards against said maxillary and mandibular teeth, respectively.

12. The sexual mouth guard of claim 11, wherein said substrate is enclosed within said top and bottom, and wherein said pivotal attachment is exposed.

* * * * *